United States Patent [19]
McCarthy

[11] Patent Number: 5,137,364
[45] Date of Patent: Aug. 11, 1992

[54] OPTICAL SPECTRAL ANALYSIS APPARATUS

[76] Inventor: Cornelius J. McCarthy, 35 Stonington Dr., Pittsford, N.Y. 14534-2923

[21] Appl. No.: 648,798

[22] Filed: Jan. 31, 1991

[51] Int. Cl.$^5$ .............................................. G01J 3/00
[52] U.S. Cl. .................... 356/402; 356/407; 250/226; 364/526
[58] Field of Search ............... 356/402, 405, 406, 407, 356/416, 419, 425; 250/226; 364/526

[56] References Cited

U.S. PATENT DOCUMENTS

| | | |
|---|---|---|
| 3,910,701 | 10/1975 | Henderson et al. |
| 3,916,168 | 10/1975 | McCarty et al. |
| 4,458,323 | 7/1984 | Willis et al. |
| 4,499,486 | 2/1985 | Farneau et al. |
| 4,505,583 | 3/1985 | Konomi . |
| 4,648,051 | 3/1987 | Wendell et al. |
| 4,654,794 | 3/1987 | O'Brien . |
| 4,834,541 | 5/1989 | Yamaba . |
| 4,881,811 | 11/1989 | O'Brien . |
| 4,937,637 | 6/1990 | Magistro . |
| 4,957,363 | 9/1990 | Takeda . |

FOREIGN PATENT DOCUMENTS 63-14224  1/1988  Japan .

OTHER PUBLICATIONS

F. Grum, C. J. Bartleson, Optical Radiation Measurements, vol. 2, 1980, Academic Press (pp. 33–47, 146).

Primary Examiner—F. L. Evans
Attorney, Agent, or Firm—M. Lukacher

[57] ABSTRACT

Apparatus for low cost measurement of light energy in terms of multiple spectral integrations with differing wavelength-dependent weights for consistency of measurements in spite of variations in component characteristics or temperature.

24 Claims, 5 Drawing Sheets

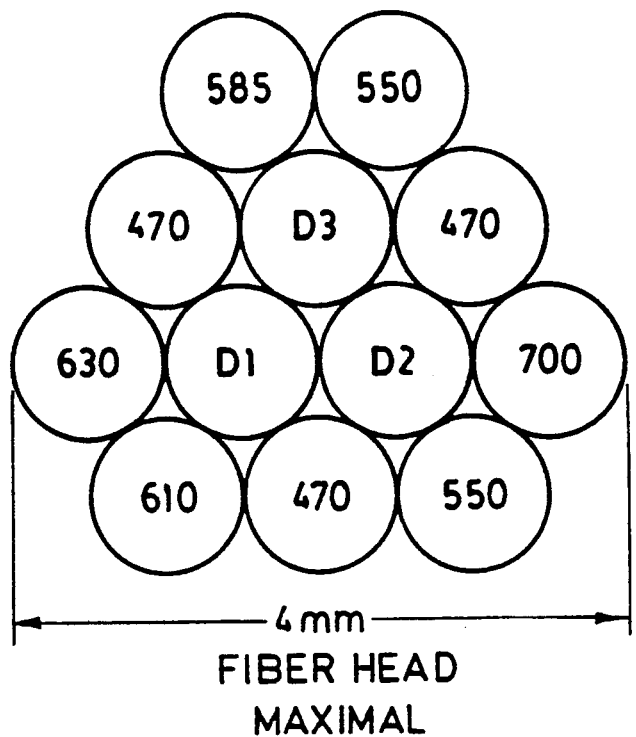
FIG.2 FIBER HEAD MAXIMAL
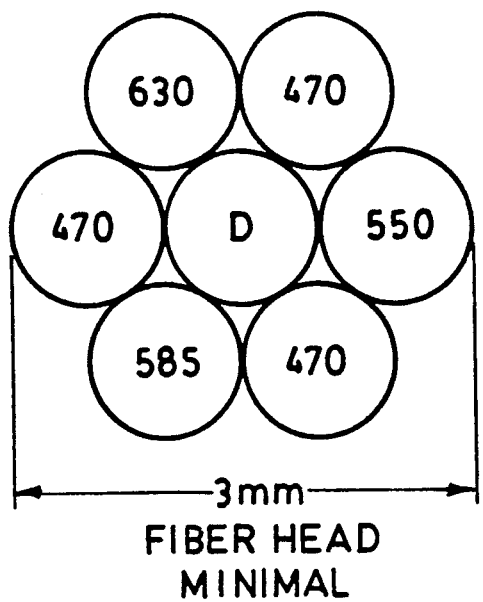
FIG.3 FIBER HEAD MINIMAL

OPTICAL SPECTRAL ANALYSIS APPARATUS

Although the human visual system is highly capable of the perception of spectral energy as brightness and color or color difference, it is less capable when used for quantification and recall. A series of instruments, generally called densitometers, colorimeters, spectrophotometers, radiometers, and chroma meters have been developed to perform these functions. This invention relates to measurement instruments which can provide high quality measurements of this class at low cost, and particularly to optical spectral analysis appratus incorporating a plurality of solid state radiation sources, such as light emitting diodes, and a plurality solid state radiation detectors.

BACKGROUND

Densitometers, colorimeters, spectrophotometers, radiometers and chroma meters all perform the same type of physical measurement. They each calculate one or more weighted integrations of optical energy over wavelength. In the case of densitometers, colorimeters, some radiometers and chroma meters, a small number of weighted integrations are normally performed. The weighting function for densitometers and colorimeters is usually the product of the spectral intensity of a light source, a filter, the sensitivity profile of a detector, and the reflection or transmission of a sample.

For chroma meters and radiometers the sample is a radiant source, and the weighting function is the product of the spectral intensity of the source, a filter parameter, and the spectral sensitivity of a detector. In the current practice for measurement of reflectance or transmission, the light source is a broad band emitter such as a tungsten lamp, and the detector has wide range of sensitivity. In general the same light source and detector profiles are used for each weighted integration and only the filter profile changes. These instruments are usually calibrated in use by using a sample of known transmittance or reflectance. Spectrophotometers and spectral radiometers are generally capable of reporting tens to thousands of weighted integrations For spectrophotometers and spectral radiometers, the weighting functions usually each have a common shape which is ideally a narrow triangle. Multiple weighted integrations are obtained by choosing multiple positions for the center of the weighting function along the wavelength axis. Spectrophotometers generally use broad band light sources and detectors, but because they may span a greater wavelength range, they may have multiple sources or detectors. The weighting function is provided by continuous filters, by multiple filters, by monochromators, by spectrographs, or by interference techniques. Densitometers, colorimeters and chroma meters are designed to produce specific weighed integrations. For densitometers used in graphic arts, the weighting of the integrations is intended to optimize the response to the reflectance of standard inks used in printing. For colorimeters and chroma meters the weighting of the integrations is intended to generate chromaticity coordinates as defined by CIE or ASTM. Spectrophotometers and spectral radiometers are intended to allow the reflectance, transmittance or intensity spectrum with reference to wavelength of the sample to be represented as a set of points, or a curve, or a spectrum. As all of these weighted integrations are linear sums over wavelength, each integration may be considered to be a vector in a common vector space. A particular set of weighted integrations will correspond to a collection of vectors from this space which form a subspace. Such subspaces are said to be spanned by the set of weighted integrations from which their component vectors may be calculated. In these terms each type of instrument can be said to measure the subset of the space which is spanned by the vectors represented by its weighted integrations. In general, the weighted integrations designed into densitometers, colorimeters, and chroma meters span a subset of the space which is spanned by the weighting functions designed into spectrophotometers and spectral radiometers. When colorimeters, densitometers, and chroma meters are designed to published standards, the specified integrations are stated in terms of sums over spectra, and these instruments are usually calibrated against the measurements of a high grade spectrophotometer or spectral radiometer or against samples for which the relectance, transmission, or spectral intensity as a function of wavelength has been independently determined. Given that each set of these weighted integrations can be expressed as subsets of the same vector space it follows that any set of weighted integrations can be transformed into any other set within the subset of the space spanned by both sets, and further it follows that this calculation will be a linear transformation which may be performed as a matrix multiplication. This is what occurs when chromaticity coordinates or densities are calculated from spectral data produced by a spectrophotometer or spectral radiometer. It also follows that there will be a collection of other sets of weighted integrations which will span the subset of the space spanned by chromaticity coordinates and by density specifications. Any such subset may be measured and used to calculate chromaticity coordinates or density functions.

SUMMARY OF THE INVENTION

Apparatus is provided which is capable of performing any type of linear transformation on a small number of inputs. The apparatus is designed to measure any set of weighted integrations, from which the desired results can be calculated. More particularly, it has been discovered in accordance with this invention that a set of weighted integrations can be selected based on consideration of cost and apparatus quality rather than on conformance to the weighting functions for which the apparatus will report measurements. A set of weighted integrations may be created which span as large a subset of the vector space as practical with the smallest number of inexpensive components. For measurement of reflectance and transmission in the optical spectral analysis apparatus according to this invention, a small number of illumination sources, each of which provides optical energy over a subset of the wavelength range of interest, and a small number of detectors, each sensitive to the entire wavelength range but each with a differently weighted sensitivity as a function of wavelength, are used. Each illumination source is made to illuminate the sample material in turn and light from the sample is directed to all detectors and detector output is recorded. Then after sequencing through all illumination sources a set of weighted integrations is derived whose number is equal to the product of the number of illumination sources times the number of detectors The weighting functions of these integrations will be the products of the individual illumination weightings functions with the individual detector sensitivity functions.

In the preferred implementations of apparatus for the measurement of reflection and transmittance the illumination sources are light emitting diodes, and the detectors are photodiodes which have been processed, treated, or filtered to produce different sensitivity curves as a function of wavelength.

The following table lists a series of configurations.

| Illum Sources | Photo Diodes | Integrations | Possible Calculations |
|---|---|---|---|
| 1 | 1 | 1 | One Axis Accept/Reject |
| 2 | 1 | 2 | Whiteness, Yellowness |
| 3 | 1 | 3 | One Illuminant Chromaticity |
| 4 | 1 | 4 | Four axis density |
| 4 | 2 | 8 | Multi Illuminant Chromaticity |
| 6 | 3 | 16 | Low resolution spectra |
| 6 | 4 | 24 | Medium resolution spectra |

In the preferred implementation the light emiting diodes (LED's), and the detectors can be in the form of unmounted semiconductor chips. For reflectance applications, the selected collection of detectors and LED's are mounted on a common substrate. At a constant temperature and when protected from humidity, light emitting diodes and photodiodes are stable devices. Therefore, a temperature sensor and optionally temperature control components are mounted on the substrate. The entire assembly is then sealed against humidity to achieve then the sensor output is used to compensate for temperature change by adjusting the linear transformation between weighted integrations and reported output units. In reflectance measurement applications, a physical shield is used to keep direct light from the LEDs from reaching the detectors and the entire assembly may be pointed at the sample surface with no optical components other than a protective seal of epoxy.

In practice the LED's for the red end of the visible wavelength range are more efficient than LED's for the blue end. Although electronic compensation would be included, it may be desirable to balance the system by using more LED chips at lower wavelengths to increase the light output in that spectral region. Thus, the invention may be implemented with six illumination sources may have more than six LED chips because of the need for duplication for some wavelengths.

For precise sampling of small areas a fiber assembly may be used. In this case a small number of short optical fibers are used to direct light from the LED's to the sample and return light to the detectors. Since the objective is to achieve a small sampling area, fibers with a thin clading layer and thus a large core diameter to clad diameter are utilized. One end of the fibers would be placed in direct contact with the detectors and LED's. Optical epoxy would be applied to ensure optical coupling, and support epoxy would hold the fiber assembly rigid. FIGS. 2 and 3 show the ends of fiber assemblies for preferred implementations. FIG. 4 shows a side view of an assembly. Special combinations of detector and illumination weighting functions can also be used to calculate factors which are not simple weighted integrations of relflectance or transmission. If one of the detectors is conditioned so that it is not sensitive to illumination at wavelengths emitted by one of the illumination sources, then response from that detector (when only that one illumination source is active) may be a measure of fluorescence by the sample.

BRIEF DESCRIPTION OF THE DRAWINGS

FIGS. 2 & 3 are end views of optical fiber assemblies which may be used to optically couple an emitter detector assembly similar to FIG. 1 to a reflectance sample.

DETAILED DESCRIPTION

Figure 1A:
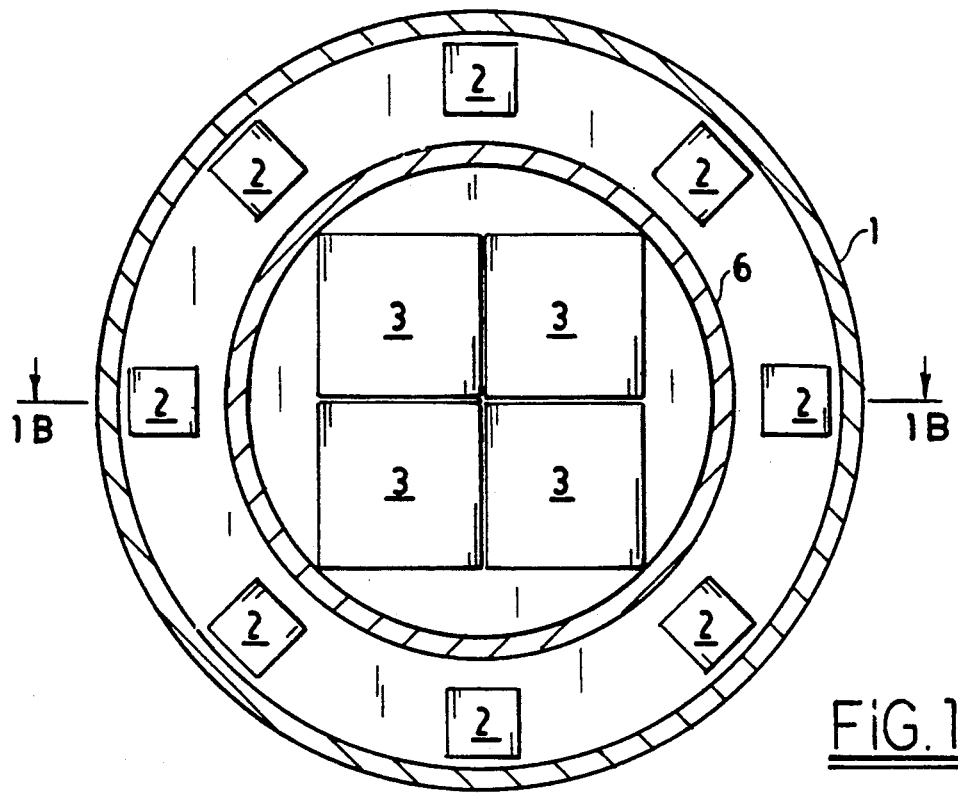
FIGS. 1a & 1b are respectively top and sectional (along 1b—1b in FIG. 1a) views of the emitter/detector assembly of an optical spectral analysis apparatus for reflectance embodying the invention
Figure 1B:
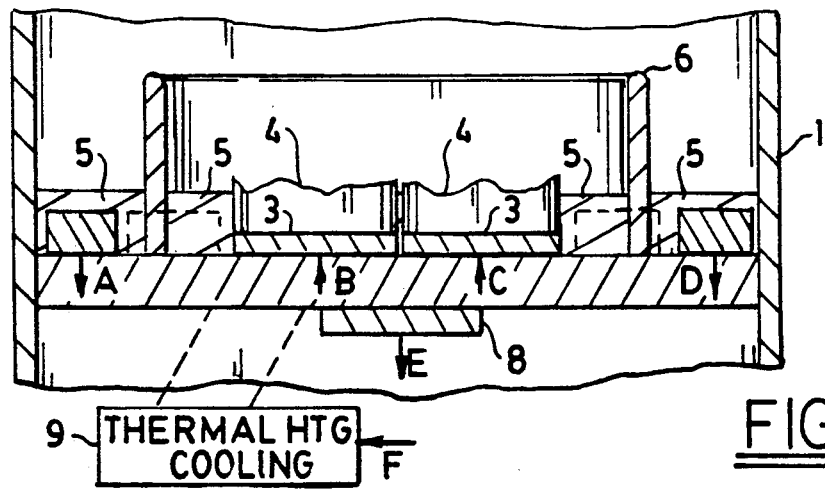

FIG. 1 shows a top view and a center section side view of an assembly of detectors and emitters for direct illumination and viewing. Item 1 is a protective outer shell 1. This shell serves, 1) to block external light, 2) to reflect light diverging outward from the emitters 2 toward the center, and 3) to contain the optical epoxy 5 over the emitters. A set of emitters in the form of LED dice 2 are distributed around the circumference of the assembly. Detectors 3 with optional filtering layers 4 are centered in the assembly. A cylinder of opaque material 6 serves to block direct light from the emitters 2 from reaching the detectors 3 and to contain optical epoxy 5. The optical epoxy 5, is applied over the emitters and detectors so that it forms a hermitic seal and so that its top surface is plane. A substrate 7 carries electrical connections and provides thermal contact between the emitters 2, the detectors 3, and a optional thermal sensing element 8.

FIG. 2 shows the sample end view and assignments for a fiber assembly with eight illumination fibers and three detector fibers. These are preferably fibers one millimeter diameter so that the maximum width of the sample end of the fiber assembly is four millimeters. The detector fibers are centered and labeled D1, D2, and D3. The illumination fibers are around the circumference of the assembly and are labeled with the center wavelength in nanometers of a corresponding light emitting diode. The lower wavelengths, 470 nanometers (nm) and 555 nm, are repeated in this pattern.

FIG. 3 shows the sample end view and assignments for a fiber assembly with six illumination fibers and one detector fiber. The one detector fiber, labeled D is optically coupled to two detectors. The illumination fibers surround the detector fiber. These are labeled by the center wavelength in nanometers of the illuminating light emitting diode. The lowest wavelength, 470 nm, is repeated three times for a total of four illumination profiles.

Figure 4:
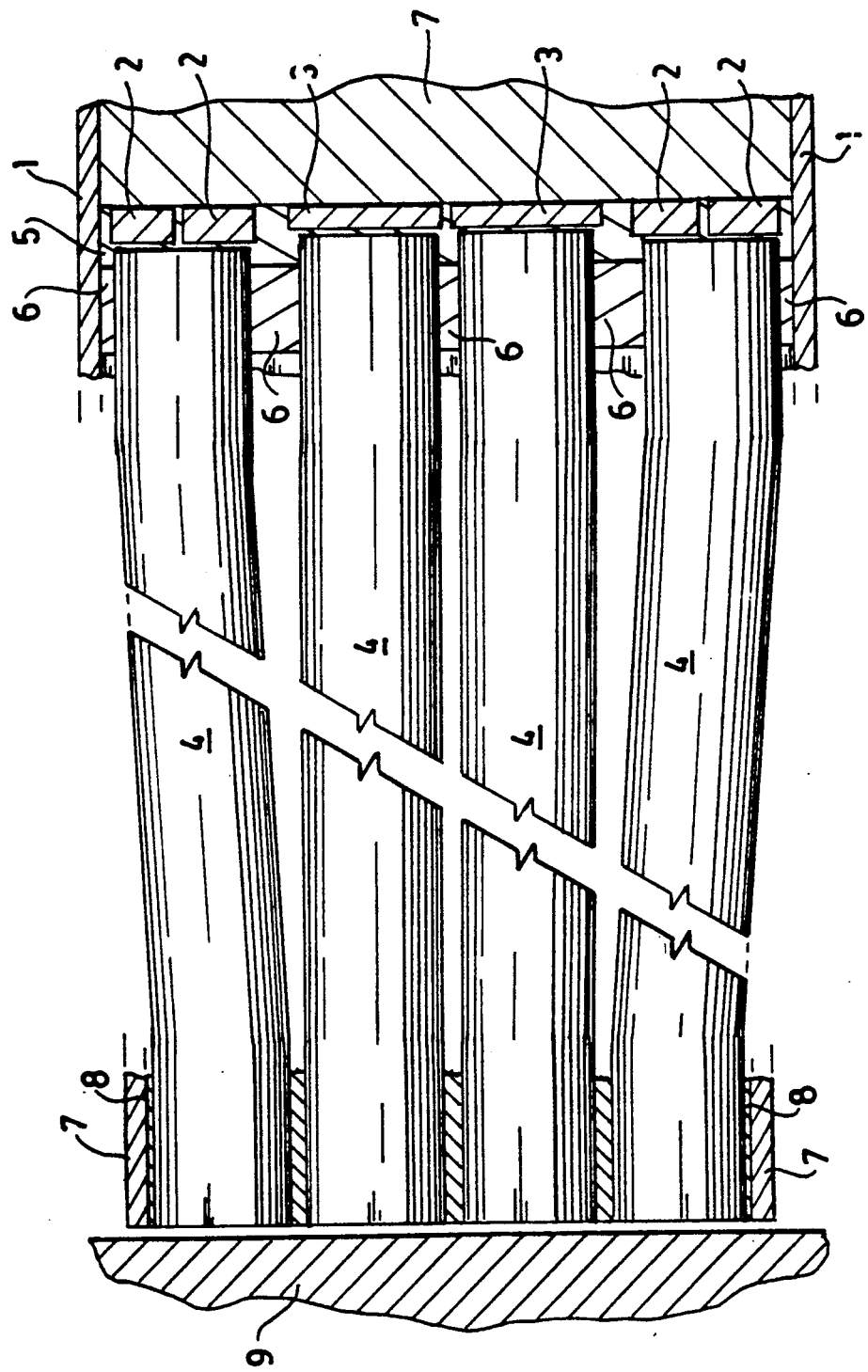
FIG. 4 is a side view of an a fiber assembly similar to FIG. 2 or FIG. 3.

FIG. 4 shows a side view of the fiber assembly. Optical fibers 4 run from the substrate 7, which mounts the emitters 2 and the detectors 3 to the sample 9). Optical epoxy 5 couples the fibers 4 to the emitters 2 and the detectors 3. Support epoxy is used to pot the assembly at the emitter detector end 6 and at the sample end 8. Outer shells at the emitter detector end 1 and at the sample end 7 protect the assembly and provide the outer boundary for the support epoxy.

Calibration using a programmable computer, built in or as a separate element, is part of the apparatus of the invention. There may be several classes of instrument calibration. Calibration is meant to be a part of a mathematical calculation to be performed using measured weighted integrations as input and generating specific user coordinates. User coordinates are the weighted integrations the instrument will report to the user. Chromaticity coordinates are an example of user coordinates. There are several classes of calibration given consideration in implementing calibration.

1) The instrument (i.e., the apparatus) may function without calibration and without stabilization. For this case the transformation from measured integrations to user coordinates would be determined as part of the design of the instrument and would be the same for all instruments using the same type of parts to report the same user coordinates.

2) The instrument may function without calibration but with on board closed loop temperature stabilization. In this case the emitters and detectors would be maintained at a constant temperature by a closed loop thermal detector and heating and or cooling system schematically shown at 9 in FIG. 1b.

3) The instrument may function with instrument specific calibration, but without stabilization. In this case each individual instrument would be used to measure a set of reference materials, with the instrument and the material held at a constant nominal temperature. The measurements would be used to calculate an insrument specific transformation from measurement to user coordinates. This transformation would be coded into each specific instrument.

4) The instrument may function with instrument specific calibration and with temperature correction. In this case a thermal sensor in contact with the substrate mounting the emitters and detectors would report the temperature at the substate to the processor used for transformation. Transformations would then be determined at multiple temperatures as per class 3 above, and temperature compensation would be applied by selecting the proper transformation to be used.

5) Finally the instrument may function with instrument specific calibration and closed loop stabilization. This is the same as case three for an instrument with closed loop thermal control at the detectors and emitters. For some detector types, configurations, and circuits the electrical signal observed may not be strictly proportional the light energy reaching the detector. When this is the case a transformation from the observed signal to a value which is proportional to light energy is required before transformation to user coordinates. Generally at least an offset correction is required. The value of such offsets may be calculated during the measurement process by observing the electrical signal generated by each detector when no illumination sources are activated. If further correction is required it would be determined on a detector by detector basis.

Figure 1C:
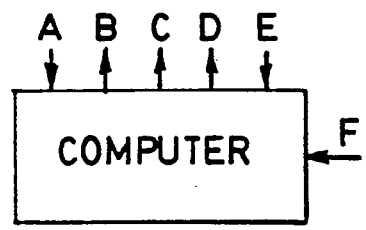
FIG. 1c shows the computer which operates the apparatus.
Figure 5A:
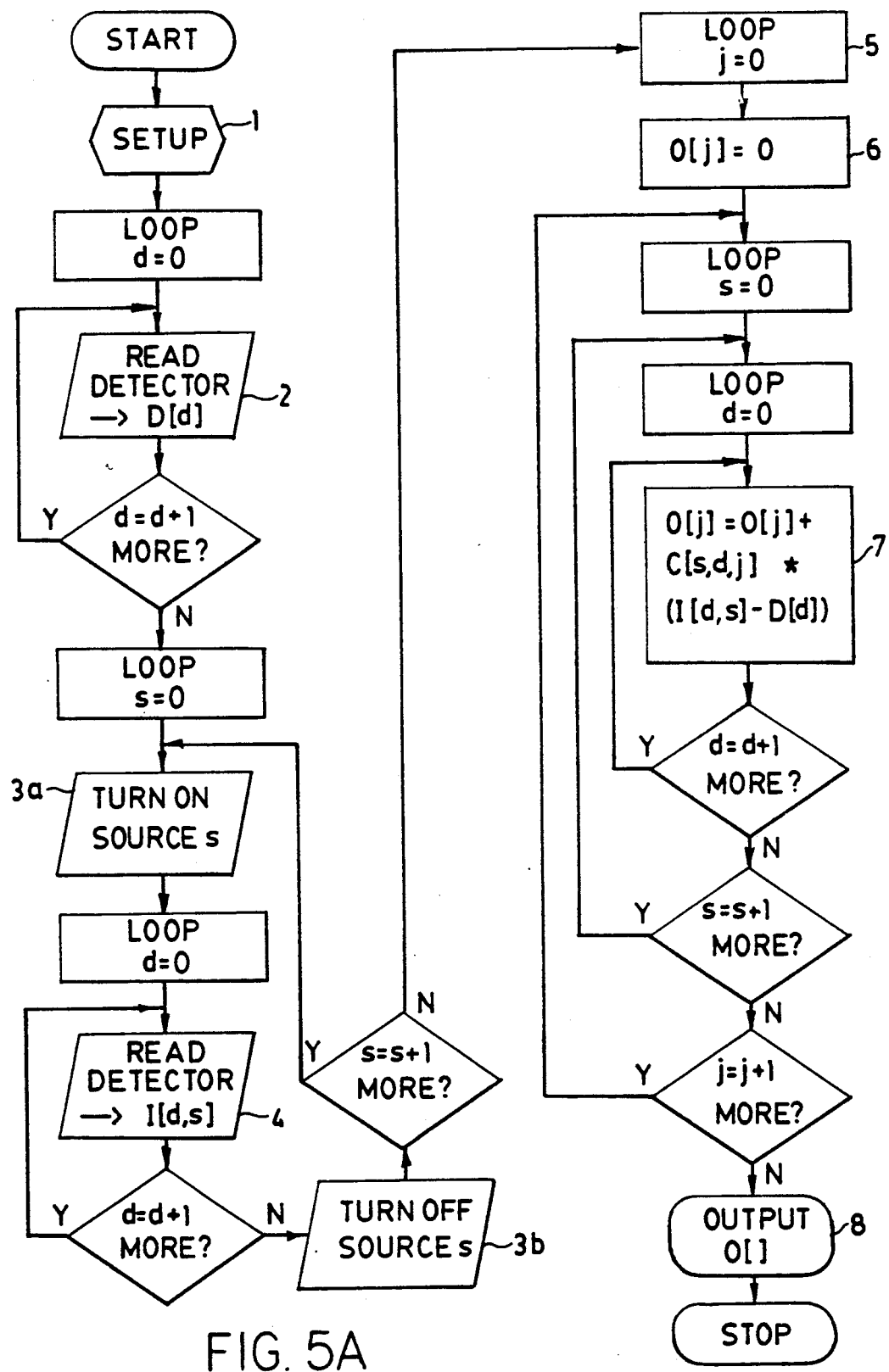
FIG. 5a & 5b are a logic flow diagram of the program, respectively for the setup and measurement operations of the apparatus which is implemented in the computer which is included in the apparatus.
Figure 5B:
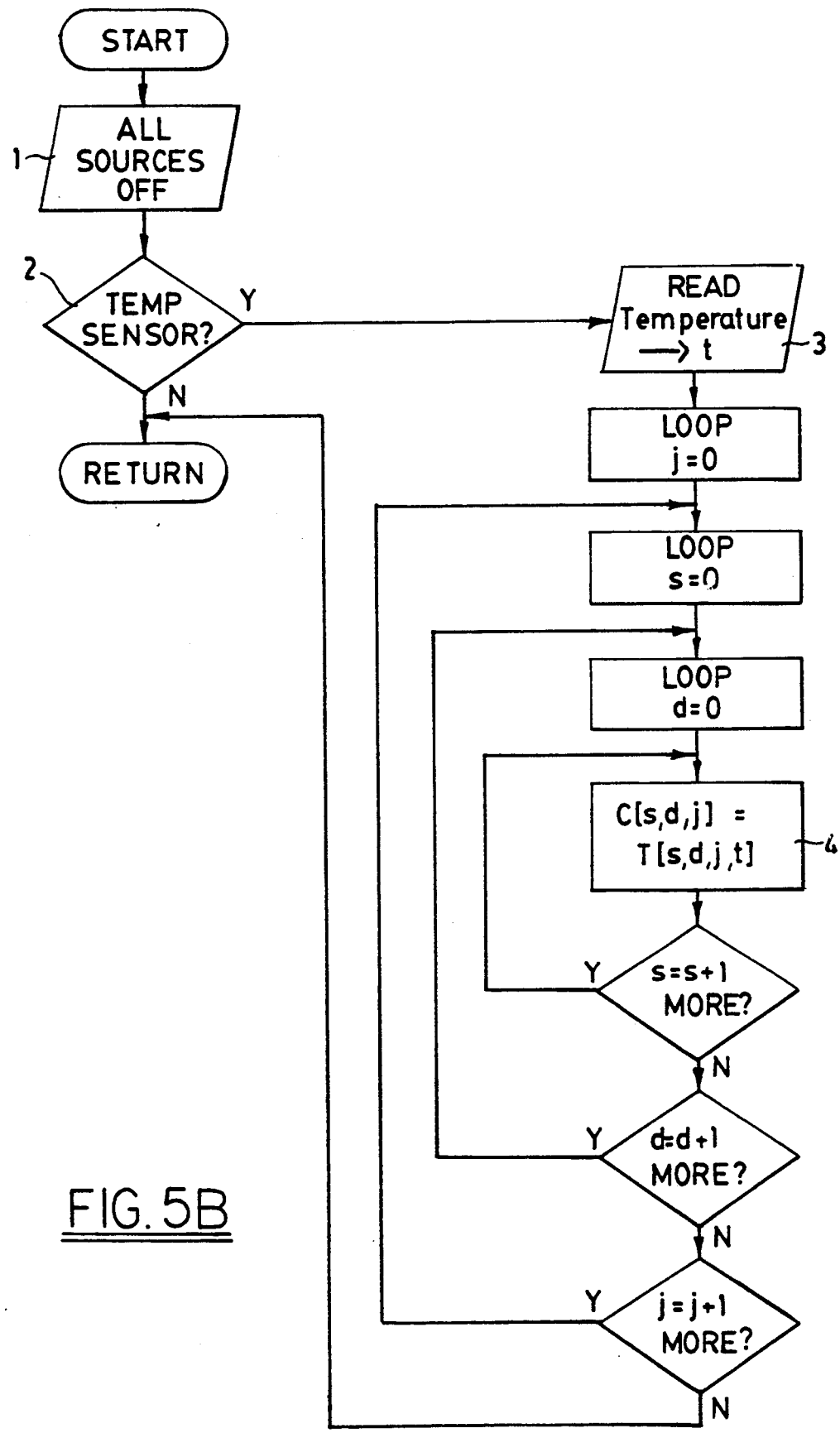

FIGS. 5a and 5b show a flow diagram for the computer program. The computer is part of the means for operating the apparatus. See FIG. 1c FIG. 5a is a measurement cycle flow diagram. A setup subroutine 1 is called first. After the setup routine a loop 2 is executed in which each detector is read with all sources off. The readings of the detectors with sources off is stored in vector D(d). When this loop is complete a double loop over sources and detector is performed. Inside the source loop each source is turned on 3a before the inner loop over detectors, and turned off 3b after the inner loop over detectors. Within the inner loop over detectors each detector is read into vector I(d,s) 4. When the double loop over sources and detectors is complete, a triple loop over output vector components, 5, sources, and detectors is performed. Within this loop the output vector O(j) is set to zero 6 and then each term of the linear transformation is added into the output vector 7. These terms are calculated as a coefficient, C(s,d,j), times the input with sources on, I(s,d), minus the reading of the detector with sources off, D(d). After the triple loop is complete, the output vector O(j) is output to the user 8.

In the setup subroutine FIG. 5b, all sources are set off 1, and the existance of a thermal sensor it tested. If no thermal sensor is present, then the coefficients of the linear transform are constants and are not modified by the setup routine. If there is a thermal sensor, then the temperature is read from the sensor 3 and a triple loop copies a set of constants T(s,d,j,t) indexed by the temperature is read into the array of coefficients C(s,d,j) 4.

The considerations which determine the programs are discussed next. Chroma meters are designed to report chromaticity coordinates for sources of light energy. The sources to be measured are generally intended for human observation, such as colored lights and signs, color television displays, and color computer display devices. Because the sample provides the light energy, the description relative to achieving lower cost by multiplexing multiple sources and multiple detectors does not apply. However, the descriptions relative to choice of weighting functions, mounting and thermal control of detectors, and calibration of measurement apparatus may be applied to an apparatus for the measurement of radiant sources. For the measurement of radiant sources, the reference material used is a set of devices of which emmitted light energy of known spectral intensities or an apparatus for producing multiple known spectra, such as a stable light source and a monochromator.

Although a multiplicity of techniques of linear algebra and numerical analysis may be used for the implementation of this invention, the following relates to the preferred implementation. Let OVECT be a vector whose components are spectral energy in each of a series of wavelength bands. For example these bands may be one nanometer wide starting at 380 nanometers and ending at 780 nanometers. In this case OVECT would have 401 components. This wavelength range and resolution would be sufficient for the mathematical description of any instrument which performed measurements which were intended to correspond to human visual judgments. Let UVECT be a vector of user coordinates. In particular, let UVECT be a set of three chromaticity coordinates as defined by the CIE. In this case UVECT would have three components. Then the definition of UVECT by the CIE may be expressed as the matrix multiplication of OVECT by a matrix of dimension 3 by 401 determined from published tables, which we will call CHROM.MAT.

$$UVECT = [CHROM.MAT] * OVECT \qquad \text{Eq.1}$$

Let DVECT be a vector whose components are weighted integrations which are produced by a given apparatus. Let APP.MAT be the matrix of weights which transforms OVECT to DVECT.

$$DVECT = [APP.MAT] * OVECT \qquad \text{Eq. 2}$$

If the vector space spanned by UVECT is a subset of the vector space spanned by UVECT then there will be a matrix which will transform DVECT to UVECT by way of matrix multiplication. We will call this matrix UAPP.MAT and write $$UVECT = [UAPP.MAT] * DVECT \qquad \text{Eq. 3}$$

For the purposes of design, we can calculate UAPP.MAT as follows:
1) Multiply Eq.2 by the transpose of APP.MAT yielding $$T[APP.MAT] * DVECT = T[APP.MAT] * [APP.MAT] * OVECT \qquad \text{Eq.4}$$

2) Multiply Eq.4 by the inverse of the product of APP.MAT with its transpose yeilding the following equation for OVECT $$OVECT = Inv(T[APP.MAT] * [APP.MAT]) * T[APP.MAT] * DVECT \qquad \text{Eq.5}$$

3) Substitute this expression in Eq.1 to obtain an equation equivalent to Eq.3.

$$UVECT = [CHROM.MAT] * Inv(T[APP.MAT] * [APP.MAT]) * T[APP.MAT] DVECT \qquad \text{Eq.6}$$

Although the equation 6 appears to be complex, in practice UAPP.MAT reduces to a collection of constants. If OVECT and DVECT each had three components then UAPP.MAT would be a 3 by 3 matrix and there would be nine constants for its components.

Current production colorimeters are designed so that DVECT is equal to UVECT, and UAPP.MAT is a unit matrix. This is neither necessary nor optimal. The number and shapes of the weighted integrations which comprise the components of DVECT may be chosento make best use of the currently available high quality low cost physical components. The selection of these components may be performed by a mathematical evaluation of the apparatus being designed using the UAPP.MAT matrix which would result from each possible selection. In preferred implementations of this invention, DVECT will generally have more components than UVECT. This generally leads to a superior resolution and noise performance in the space spanned by UVECT. These improvements can generally be achieved at a minimal increase in production cost. Resolution and noise performance in the UVECT space are predicted from assumptions in the space spanned by DVECT using UAPP.MAT.

As a part of the production process the components of UAPP.MAT may be adjusted by calibration, as discussed above, to improve the accuracy of the mapping rom DVECT to UVECT for each physical instance of the apparatus produced. In effect, this is accomplished by the application of multiple regression techniques to a set of materials for which OVECT and/or UVECT were known. The effects of thermal variation and component variation in user coordinates may be predicted if these effects are known OVECT coordinates or in DVECT coordinates.

I claim:
1. Optical spectral analysis apparatus for measurements of optical properties of a sample which comprises a plurality of sources of radiant energy, a plurality of devices for the conversion of radiant energy in to electrical signals, means in each of said sources for providing a spectrum of energy with reference to wavelength which said spectrum is different from said spectrum of the others of said sources, means in each of said devices for providing a response to radiant energy as a function of wavelength which differs from the response to radiant energy for each of the others of said devices, and means for operating said apparatus by first providing electrical energy to each said source of radiant energy, for each of distinct periods of time during which said periods of time at least one of the other sources of radiant energy is not provided with electrical energy, and second allowing or directing radiant energy produced by said sources to interact with the sample in such a fashion that some radiant energy reflected from and/or transmitted by and/or emitted by said sample is returned to said devices, and third recording the electrical signals from each said device for the conversion of radiant energy to electrical signal output during each such said period of time, and fourth calculating from each said recorded electrical signal output a value which is a weighted integration of radiant energy over wavelength, thus producing a set of said weighted integration values whose number is equal to the product of the number of said distinct time periods with the number of said devices for the conversion of radiant energy to electrical signal, and fifth calculating from said set of weighted integration values said set of multiple measurements by linear transformation of said set of weighted integration values utilizing predetermined coefficients for transformation.

2. Apparatus as per claim 1 wherein said sources are electrical to radiant energy conversion devices.

3. Apparatus as per claim 2 in wherein at least two of said devices are light emitting diodes.

4. Apparatus per claim 1 in which said sources of radiant energy and said devices for the conversion of radiant energy to electrical signal are mounted on a common substrate, which substrate provides mechanical positioning, electrical connections, and a common thermal contact.

5. Apparatus per claim 4 in which an electrical device sensitive to temperature is also mounted in thermal contact with said substrate.

6. Apparatus per claim 5 in which a device for the creation or removal of heat energy is in thermal contact with said substrate.

7. Apparatus per claim 4 in which said sources of radiant energy, and devices, and common substrate are sealed with a material which is transparent to light energy of the wavelengths of interest in the measurements performed, but impervious to moisture.

8. Apparatus per claim 1 in which said operations means have means for computing said coefficients of said linear transformation at the time of manufacture of said apparatus by recording a set of observed weighted integrations for each of a number of objects or materials with established optical characteristics, and calculating the coefficients of the linear transformation using techniques of multiple regression.

9. Apparatus per claim 8 in which a plurality of sets of said coefficients are computed each said set being determined while said apparatus is maintained at a temperature different from the temperature maintained during the determination of each other said set, and said operating means having means for the selection of a particular set of coefficients from said plurality of sets as a function of temperature.

10. Apparatus per claim 9 in which said operating means includes means for the selection of said coefficients of linear transformation as a function of temperature by interpolation between said sets of coefficients.

11. Apparatus per claim 1 in which radiation is directed to said sample from said sources by multiple optical fibers, which fibers have a core diameter which is at least 90% of their clad diameter.

12. Apparatus per claim 1 in which radiation is directed from the sample to said devices for the conversion of radiant energy to electrical signal by optical fibers.

13. Apparatus per claim 11 in which said optical fibers are rigidly positioned.

14. Apparatus per claim 11 in which a plurality of semiconductor chips, provide said sources of radiant energy and said devices said chips being in physical contact with said optical fibers.

15. Apparatus for the determination of multiple measurements of radiant energy emitted by a sample comprising multiple devices for the conversion of radiant energy to electrical signal, means for optical coupling said devices to said sample, means in said multiple devices for the conversion of radiant energy to electrical signals so that each said device for the conversion of radiant energy to electrical signal has a response to optical energy as a function of wavelength which differs from the response to radiant energy for the other of said devices, and means for operating said apparatus including first means for observing and recording the electrical output of each of said devices for the conversion of radiant energy to electrical signal, second means for calculating from each said recorded electrical output a value which is a weighted integration of radiant energy over wavelength to produce a set of weighted integration values, and third means for calculating from such set of said weighted integration values said set of multiple measurements by linear transformation with pre-determined coefficients of such set of weighted integration values.

16. Apparatus per claim 15 in which said devices for the conversion of radiant energy to electrical signal are mounted on a common substrate, which substrate provides mechanical positioning, electrical connections, and a common thermal contact.

17. Apparatus per claim 16 in which an electrical device sensitive to temperature is also mounted in thermal contact with said substrate.

18. Apparatus per claim 17 in which a device for the creation or removal of heat energy is in thermal contact with said substrate.

19. Apparatus per claim 16 in which said devices and common substrate are sealed with a material which is transparent to light energy of the wavelengths of interest in the measurements performed, but impervious to moisture.

20. Apparatus per claim 15 in which said operating means includes means for computing the coefficients of said linear transformation operation at the time of manufacture of said apparatus by recording a set of observed weighted integrations for each of a number sources with established optical characteristics and calculating the coefficients of the linear transformation using techniques of multiple regression.

21. Apparatus per claim 20 wherein said computing means including means for computing a plurality of sets of said coefficients, each of said sets while said apparatus is maintained at a temperature different from the temperature maintained during the computing of each other set, and means for incorporating into said third means a particular set of coefficients from said plurality of sets as a function of temperature at which said apparatus is operating.

22. Apparatus per claim 21 in which said operating means includes means for the selection of said coefficients of linear transformation as a function of temperature by interpolation between said sets of coefficients.

23. Apparatus per claim 15 in which radiation is directed from said sample to said devices by multiple optical fibers, which fibers have a core diameter which is at least 90% of their clad diameter.

24. Apparatus per claim 23 in which said optical fibers are rigidly positioned.

* * * * *